United States Patent
Garlock et al.

(10) Patent No.: US 10,617,440 B2
(45) Date of Patent: Apr. 14, 2020

(54) SYSTEMS AND METHODS FOR PERFORMING ENDOSCOPIC RELEASE PROCEDURES

(71) Applicant: ARTHREX, INC., Naples, FL (US)

(72) Inventors: Adam Garlock, Naples, FL (US); Zachary Day, Naples, FL (US); Phinit Phisitkul, Coralville, IA (US); Annuziato Amendola, Durham, NC (US)

(73) Assignee: ARTHREX, INC., Naples, FL (US)

( * ) Notice: Subject to any disclaimer, the term of this patent is extended or adjusted under 35 U.S.C. 154(b) by 242 days.

(21) Appl. No.: 15/670,019

(22) Filed: Aug. 7, 2017

(65) Prior Publication Data

US 2018/0042631 A1 Feb. 15, 2018

Related U.S. Application Data

(60) Provisional application No. 62/373,585, filed on Aug. 11, 2016.

(51) Int. Cl.
*A61B 17/32* (2006.01)
*A61B 17/3211* (2006.01)

(52) U.S. Cl.
CPC .. *A61B 17/320016* (2013.01); *A61B 17/3211* (2013.01); *A61B 17/320036* (2013.01); *A61B 2017/320044* (2013.01); *A61B 2017/320052* (2013.01)

(58) Field of Classification Search
CPC ........ A61B 17/3211; A61B 17/320016; A61B 17/3207; A61B 17/22; A61B 2017/320044; A61B 2017/320052; A61B 2017/320056; A61B 17/320036
See application file for complete search history.

(56) References Cited

U.S. PATENT DOCUMENTS

| | | | |
|---|---|---|---|
| 5,323,765 A * | 6/1994 | Brown | A61B 17/320036 128/898 |
| 5,325,883 A * | 7/1994 | Orr | A61B 17/320036 128/898 |
| 5,651,790 A * | 7/1997 | Resnick | A61B 17/1659 606/167 |
| 5,827,312 A | 10/1998 | Brown et al. | |
| 6,685,630 B2 | 2/2004 | Sauer et al. | |
| 7,041,115 B2 | 5/2006 | Mirza et al. | |
| 7,470,230 B2 | 12/2008 | Smith et al. | |
| 8,202,290 B2 | 6/2012 | Smith | |
| 8,821,383 B2 | 9/2014 | Mirza et al. | |
| 2007/0288043 A1 * | 12/2007 | Rehnke | A61B 1/313 606/170 |
| 2012/0296359 A1 * | 11/2012 | Mire | A61B 17/3421 606/191 |
| 2017/0252056 A1 * | 9/2017 | Garvey | A61B 1/0014 |

* cited by examiner

*Primary Examiner* — Tuan V Nguyen
(74) *Attorney, Agent, or Firm* — Carlson, Gaskey & Olds

(57) ABSTRACT

Surgical systems and methods for performing endoscopic release procedures are disclosed herein. In an embodiment, a surgical system includes a plane finder probe adapted to establish a cutting plane for resecting an anatomical structure, and a slotted cannula insertable over the plane finder probe to position the slotted cannula along the cutting plane.

21 Claims, 13 Drawing Sheets

SYSTEMS AND METHODS FOR PERFORMING ENDOSCOPIC RELEASE PROCEDURES

CROSS REFERENCE TO RELATED APPLICATIONS

This disclosure claims priority to U.S. Provisional Application No. 62/373,585, which was filed on Aug. 11, 2016, the entire disclosure of which is incorporated herein by reference.

BACKGROUND

This disclosure relates to systems and methods for performing endoscopic release procedures.

Heel pain is a common ailment associated with the foot. Heel pain may be caused by excessive tightness in the gastrocnemius muscle of the calf of the leg or from irritation or scarring of the plantar fascia, which is the thick band of tissue that connects the heel to the toes. Resection or release procedures can be performed to lengthen the gastrocnemius tendon or remove diseased portions of the plantar fascia to attempt to alleviate the heel pain. These procedures have traditionally been open procedures which result in substantial trauma to the patient. Attempts to perform these procedures endoscopically have generally been unsuccessful because of the inability to visualize the anatomical structures requiring resection during the release procedure.

SUMMARY

This disclosure relates to surgical systems and methods for performing endoscopic release procedures. Exemplary endoscopic release procedures include gastrocnemius release procedures and plantar fascia release procedures.

A surgical system includes, inter alia, a plane finder probe adapted to establish a cutting plane for resecting an anatomical structure, and a slotted cannula insertable over the plane finder probe to position the slotted cannula along the cutting plane.

A method for performing an endoscopic release procedure includes, inter alia, inserting a plane finder probe into a soft tissue space to establish a cutting plane for resecting an anatomical structure, inserting a slotted cannula over the plane finder probe to position the slotted cannula along the cutting plane, removing the plane finder probe, inserting a cutting blade into the slotted cannula, and resecting the anatomical structure along the cutting plane with the cutting blade.

DETAILED DESCRIPTION

Figure 1:
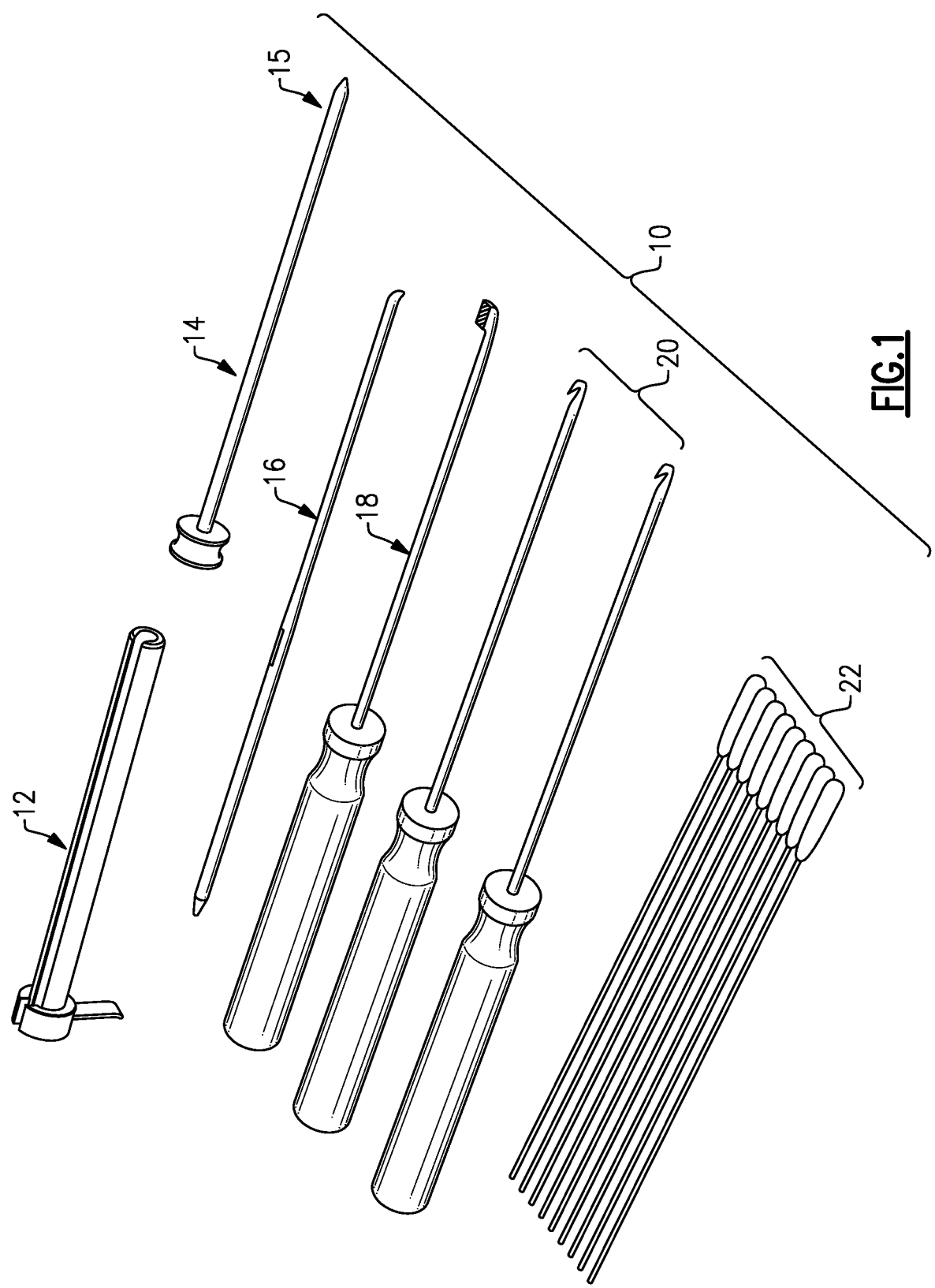
FIG. 1 illustrates a surgical system for performing an endoscopic release procedure.

This disclosure relates to surgical systems and methods for performing endoscopic release procedures, including but not limited to gastrocnemius release procedures and plantar fascia release procedures. A surgical system may be employed for performing the endoscopic release procedures. The surgical system includes at least a slotted cannula and a plane finder probe.

In some embodiments, the plane finder probe is inserted into a soft tissue space to establish a cutting plane for resecting an anatomical structure. The slotted cannula is then inserted over the plane finder probe to position the slotted cannula along the cutting plane. A cutting blade is then inserted through the slotted cannula to cut the anatomical structure along the cutting plane.

A surgical system includes, inter alia, a plane finder probe adapted to establish a cutting plane for resecting an anatomical structure, and a slotted cannula insertable over the plane finder probe to position the slotted cannula along the cutting plane.

In a further embodiment, a plane finder probe includes a probe body that extends between a blunt ended portion and an angled portion.

In a further embodiment, a probe body of a plane finder probe tapers from a blunt ended portion toward an angled portion.

In a further embodiment, a plane finder probe is positionable within a slot of a slotted cannula.

In a further embodiment, a slotted cannula is made from a transparent material.

In a further embodiment, a slotted cannula extends along a longitudinal axis between a proximal end portion and a distal end portion.

In a further embodiment, a hub is disposed at a proximal end portion of a slotted cannula and includes a central aperture sized to accommodate another surgical instrument.

In a further embodiment, a handle extends from a hub of a slotted cannula.

In a further embodiment, a trocar is insertable through a slotted cannula.

In a further embodiment, a swabbing device is insertable through a slotted cannula.

In a further embodiment, an endoscope is insertable at a first side of a slotted cannula and a cutting blade is insertable at a second side of the slotted cannula.

A method for performing an endoscopic release procedure includes, inter alia, inserting a plane finder probe into a soft tissue space to establish a cutting plane for resecting an anatomical structure, inserting a slotted cannula over the plane finder probe to position the slotted cannula along the cutting plane, removing the plane finder probe, inserting a cutting blade into the slotted cannula, and resecting the anatomical structure along the cutting plane with the cutting blade.

In a further embodiment, an endoscopic release procedure is a gastrocnemius release procedure.

In a further embodiment, an endoscopic release procedure is a plantar fascia release procedure.

In a further embodiment, the method includes, prior to inserting a plane finder probe, making a first incision at a first location associated with a soft tissue space, inserting an assembly of a trocar and a slotted cannula through the first incision, palpating skin associated with the soft tissue space using the trocar to mark a second location of a second incision, and making the second incision at the second location.

In a further embodiment, the method includes inserting an endoscope into a first side of a slotted cannula and inserting a plane finder probe into a second side of the slotted cannula.

In a further embodiment, the method includes inserting an endoscope into a first side of a slotted cannula and inserting a cutting blade into a second side of the slotted cannula.

In a further embodiment, the method includes inserting an endoscope into a second side of a slotted cannula, inserting a cutting blade into a first side of the slotted cannula, and making additional cuts in the anatomical structure with the cutting blade.

In a further embodiment, the method includes making a first incision at a first location of a soft tissue space prior to inserting a plane finder probe, inserting the plane finder probe through the first incision, palpating skin with the plane finder probe to mark a second location of a second incision, and making the second incision at the second location.

In a further embodiment, the method includes moving a plane finder probe so it extends through both a first incision and a second incision, and inserting the slotted cannula over the plane finder probe after moving the plane finder probe through both the first incision and the second incision.

FIG. 1 illustrates a surgical system 10 for performing endoscopic release procedures. Exemplary endoscopic release procedures include gastrocnemius release procedures and plantar fascia release procedures. However, the surgical system 10 of this disclosure could be utilized for various other endoscopic procedures.

The surgical system 10 includes multiple surgical instruments that may be provided as part of a surgical instrumentation set or kit. In an embodiment, the surgical system 10 includes a slotted cannula 12, a trocar 14, a plane finder probe 16, a rasp 18, one or more cutting blades 20, and multiple swabbing devices 22.

The slotted cannula 12 is used to insert and maneuver surgical instruments, such as the trocar 14 and the cutting blades 20, into a soft tissue space during an endoscopic release procedure. When used in combination with an endoscope, the slotted cannula 12 provides visualization feedback of the surrounding anatomy to the user during the endoscopic release procedure.

The trocar 14 is used to help position the slotted cannula 12 within the soft tissue space. The trocar 14 can include a tapered tip 15 to help maneuver the trocar 14 through the soft tissue and into the targeted space.

The plane finder probe 16 is used as a dissecting tool to dissect tissue within the soft tissue space and to better identify the anatomy which is to be cut, recessed, or released. The plane finder probe 16 may be inserted into the soft tissue space to establish the correct cutting plane for creating cuts in a muscle, tendon, ligament, or other anatomical structure of the soft tissue space.

The rasp 18 is used to clear fat or tissue from the soft tissue space. This helps to better prepare the anatomy for the release procedure.

The cutting blades 20 may be used to make various cuts during the release procedure. The surgical system 10 may include multiple cutting blades 20 each having a different cutting blade tip that provide the user with different cutting options during the procedure.

Finally, the swabbing devices 22 are used to clear the soft tissue space of blood, fluid, tissue, or other debris which could interfere with optimal visualization of the soft tissue space during the endoscopic release procedure. In an embodiment, the swabbing devices 22 are cotton swabs. The surgical system 10 could include any amount of the swabbing devices 22.

Figure 2:
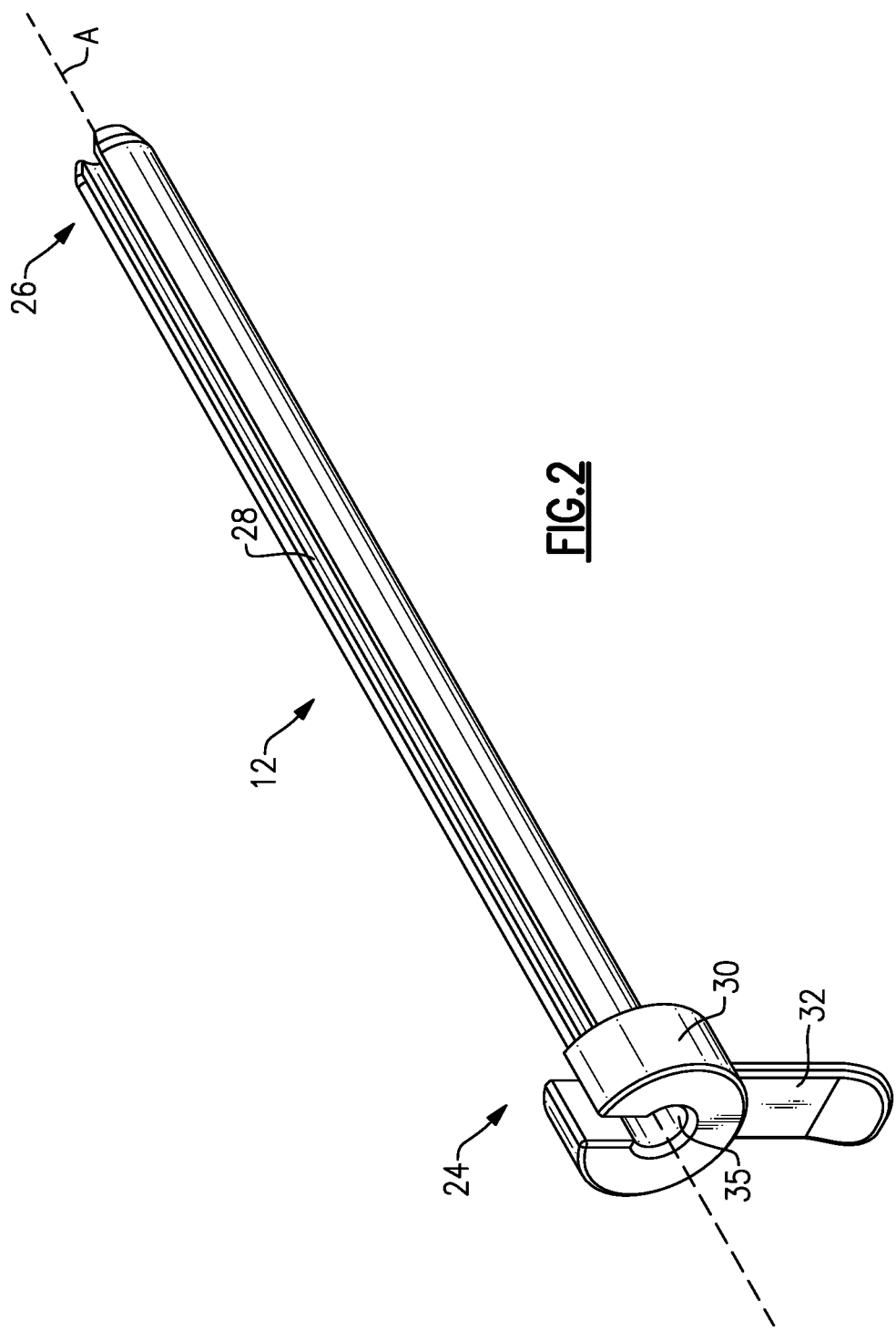
FIG. 2 illustrates a slotted cannula of the surgical system of FIG. 1.

FIG. 2 illustrates additional features of the slotted cannula 12. The slotted cannula 12 extends along a longitudinal axis A between a proximal end portion 24 and a distal end portion 26. In an embodiment, the slotted cannula 12 embodies a circular cross-section, although other cross-sectional shapes are also contemplated. A slot 28 is formed in the slotted cannula 12 and extends longitudinally from the proximal end portion 24 to the distal end portion 26.

A hub 30, or flanged portion, is positioned at the proximal end portion 24 and includes a handle 32 for gripping the slotted cannula 12. The hub 30 further includes a central aperture 35 sized to accommodate the passage of various surgical instruments through the slotted cannula 12.

In another embodiment, the slotted cannula 12 is made from a transparent material. The transparent material may be a transparent plastic material that permits the transmission of light through the slotted cannula 12. The transparency of the slotted cannula 12 permits the direct visualization of the anatomical structures surrounding the sotted cannula 12 via an endoscope during the endoscopic release procedure.

Figure 3:
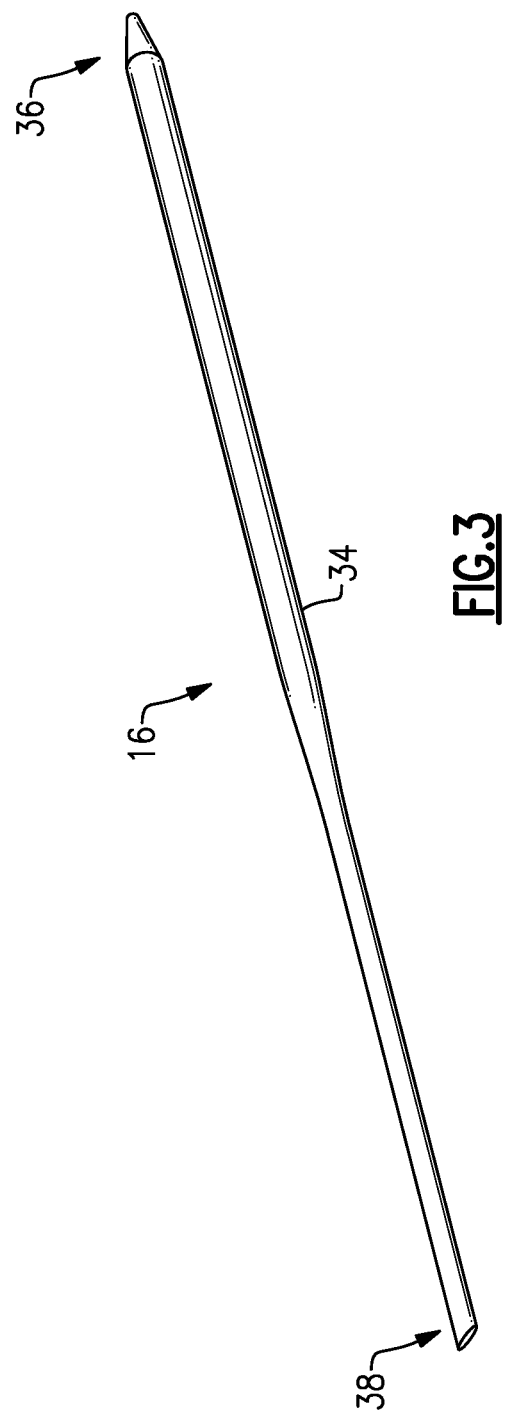
FIG. 3 illustrates a plane finder probe of the surgical system of FIG. 1.
Figure 4:
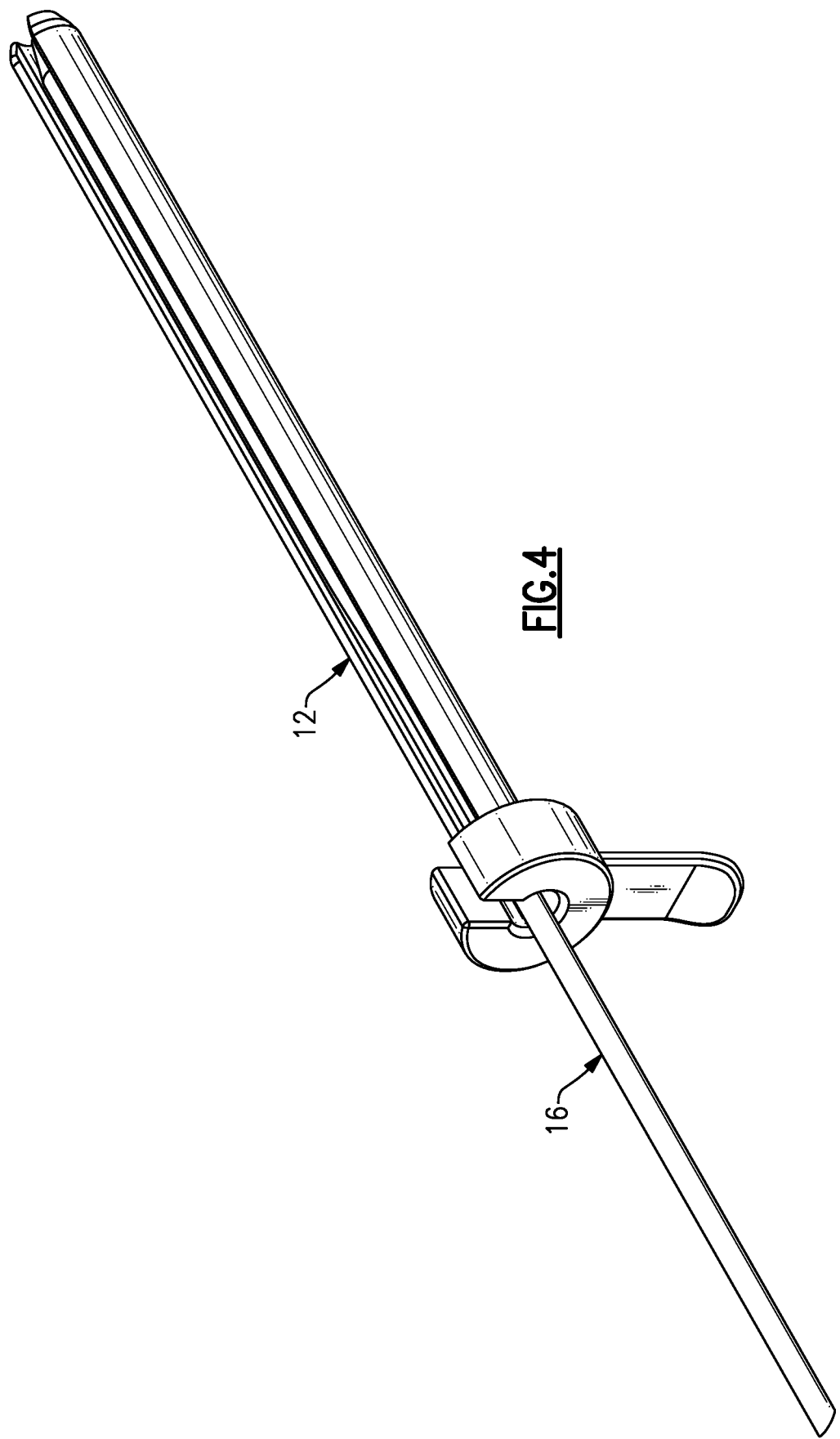
FIG. 4 illustrates an assembly of the slotted cannula of FIG. 2 and the plane finder probe of FIG. 3.

FIG. 3 illustrates additional features of the plane finder probe 16. The plane finder probe 16 includes a probe body 34 that extends longitudinally between a blunt ended portion 36 and an angled portion 38. The probe body 34 may slightly taper from the blunt ended portion 36 toward the angled portion 38. The plane finder probe 16 is positionable within the slot 28 of the slotted cannula 12, or the slotted cannula 12 may be received over the plane finder probe 16 (see FIG. 4).

FIGS. 5-15, with continued reference to FIGS. 1-4, schematically illustrate an exemplary gastrocnemius release procedure. These figures illustrate, in sequential order, a non-limiting embodiment for performing an endoscopic gastrocnemius release procedure. It should be understood; however, that fewer or additional steps than are recited below could be performed and that the recited order of steps is not intended to limit this disclosure. In an embodiment, the gastrocnemius release procedure is an endoscopic procedure.

Figure 5:
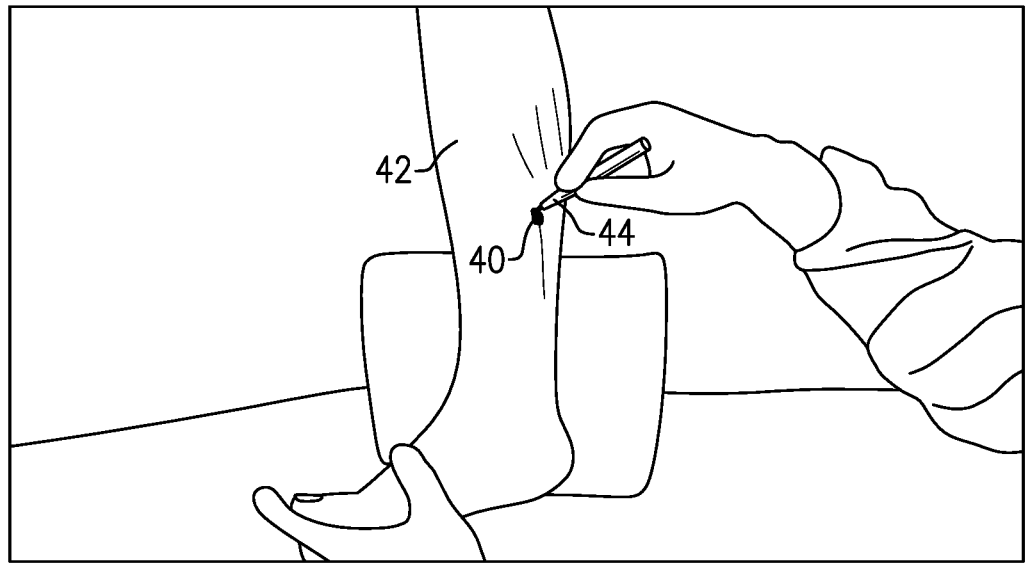
FIGS. 5, 6, 7, 8, 9, 10, 11, 12, 13, 14, and 15 schematically illustrate an exemplary gastrocnemius release procedure.

Referring first to FIG. 5, a medial incision 40 is made in a patient's lower leg 42 using a scalpel 44 or some other cutting device. The medial incision 40 may be made just below the gastrocnemius-soleus muscle junction. This location may be marked on the lower leg 42 prior to making the medial incision 40.

Figure 6:
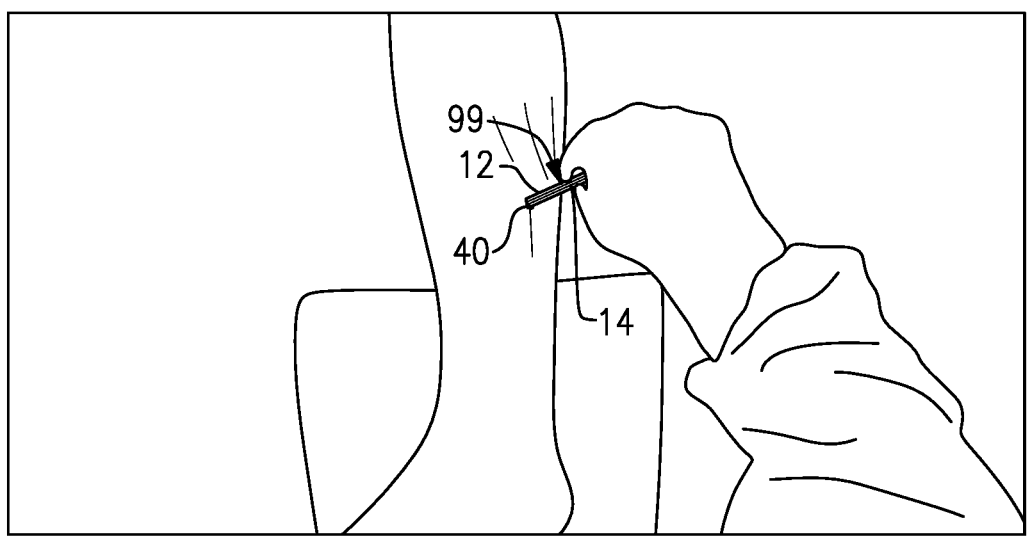
Figure 7:
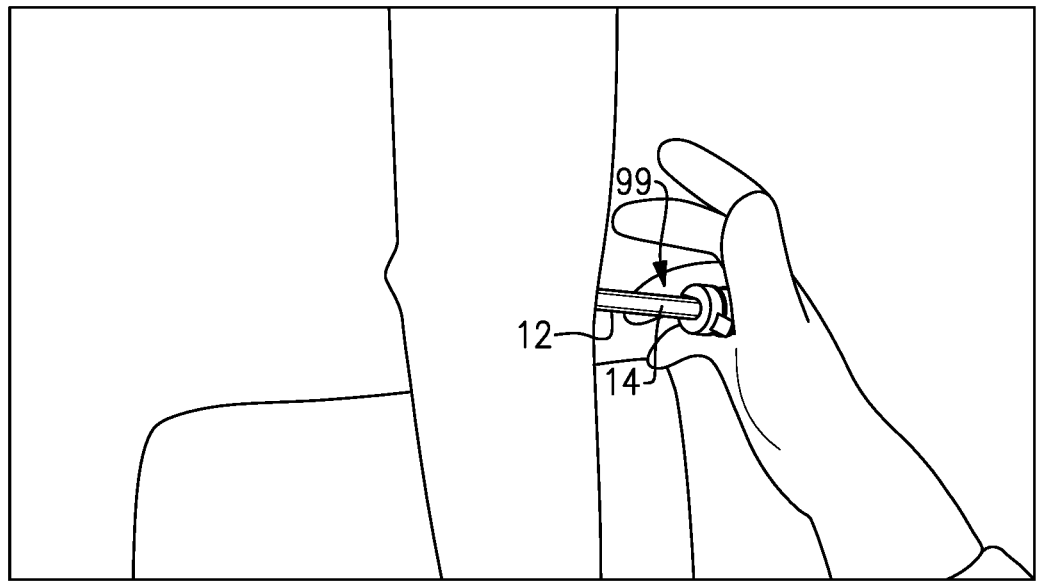
Figure 8:
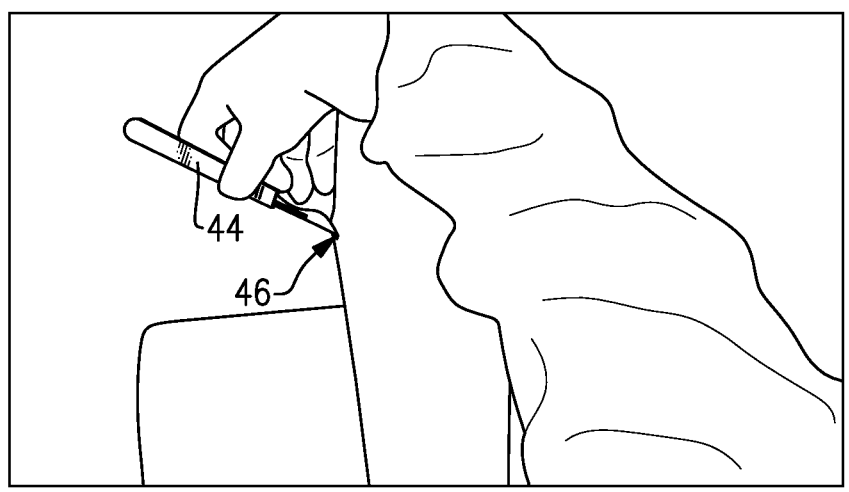

Next, as shown in FIGS. 6 and 7, an assembly 99 of the trocar 14 and the slotted cannula 12 is inserted through the medial incision 40 and then moved laterally until the trocar 14 has reached the opposite side of the soft tissue space (i.e., just under the skin on the lateral side of the lower leg 42). The tip of the trocar 14 may be used to palpate the skin (see FIG. 7) to mark the location for creating a lateral incision 46. The scalpel 44 is then used to create the lateral incision 46 (see FIG. 8).

Figure 9:
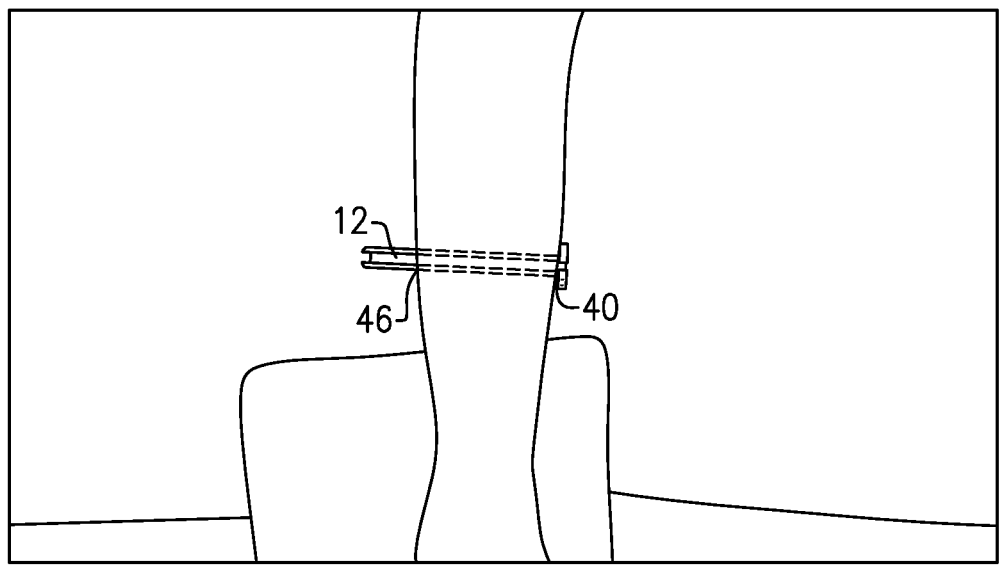

Referring next to FIG. 9, the slotted cannula 12 is moved further laterally such that it extends through both the medial incision 40 and the lateral incision 46. This movement fully positions the slotted cannula 12 through the soft tissue space. The trocar 14 may then be removed.

Figure 10:
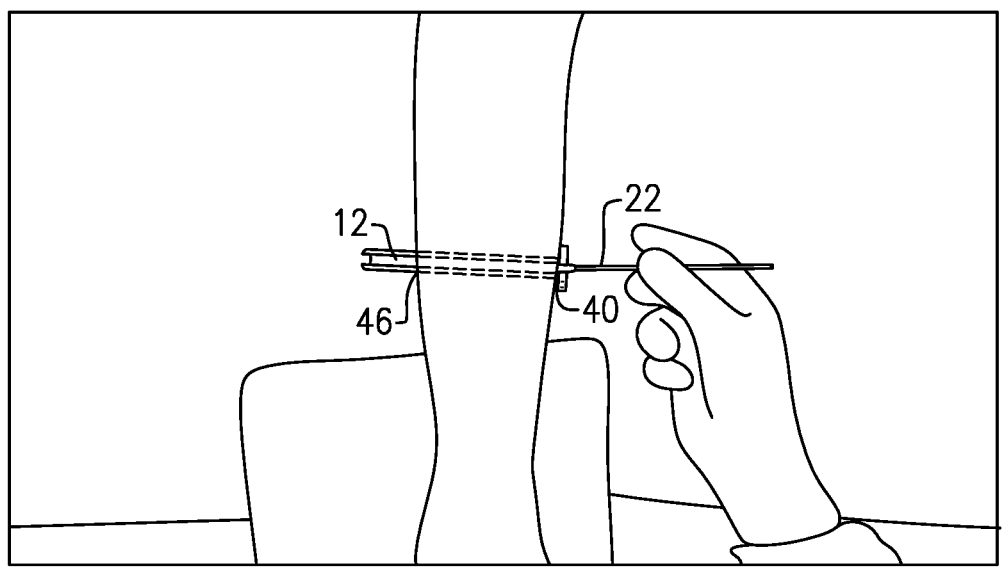

As shown in FIG. 10, the swabbing devices 22 may be used to clean the soft tissue space of any fluid, tissue, blood, etc., that could inhibit visualization during the procedure. The swabbing devices 22 are passed in a single direction through the slotted cannula 12 (here, medially to laterally) to avoid leaving any debris within the soft tissue space.

Figure 11:
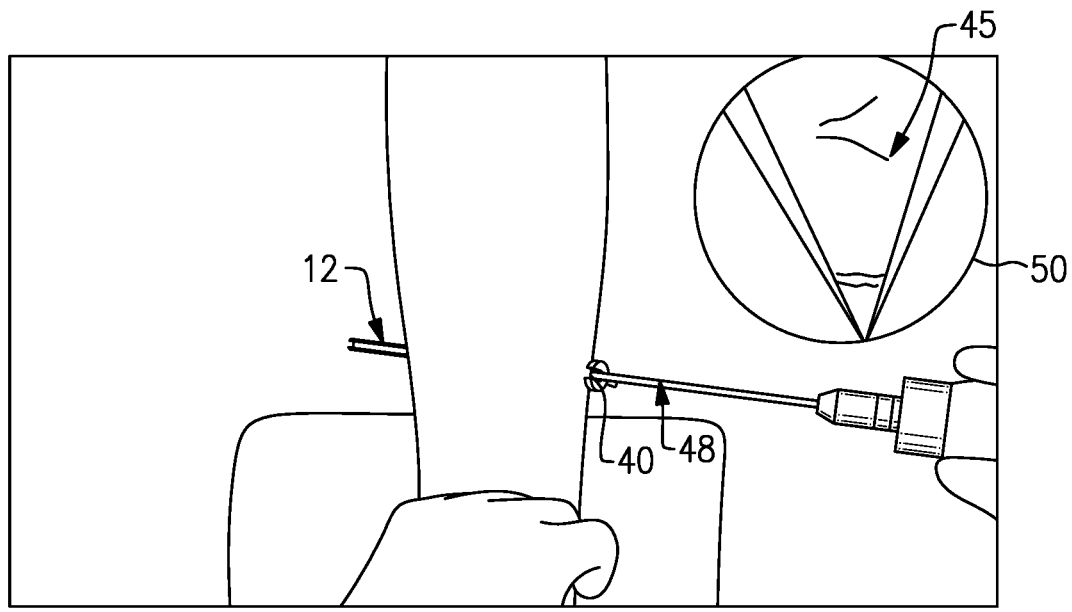

An endoscope 48 is next inserted into the slotted cannula 12 on the side of the medial incision 40 (see FIG. 11). The endoscope 48 provides direct visualization of the soft tissue space 45, via an arthroscopic window 50, through the translucent, slotted cannula 12.

Figure 12:
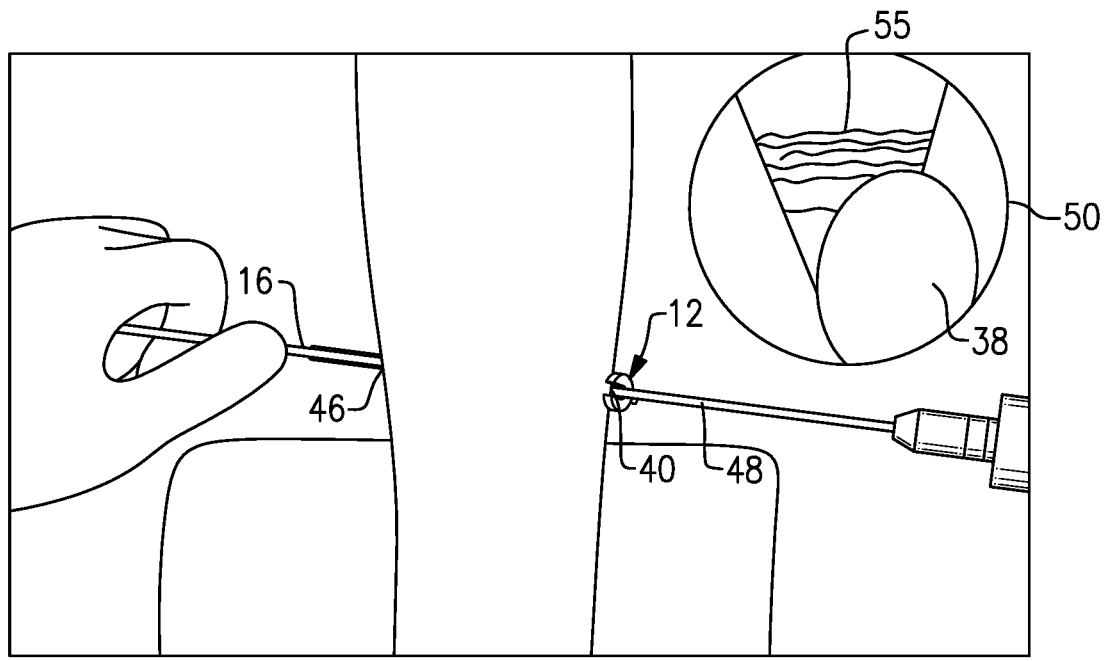
Figure 13:
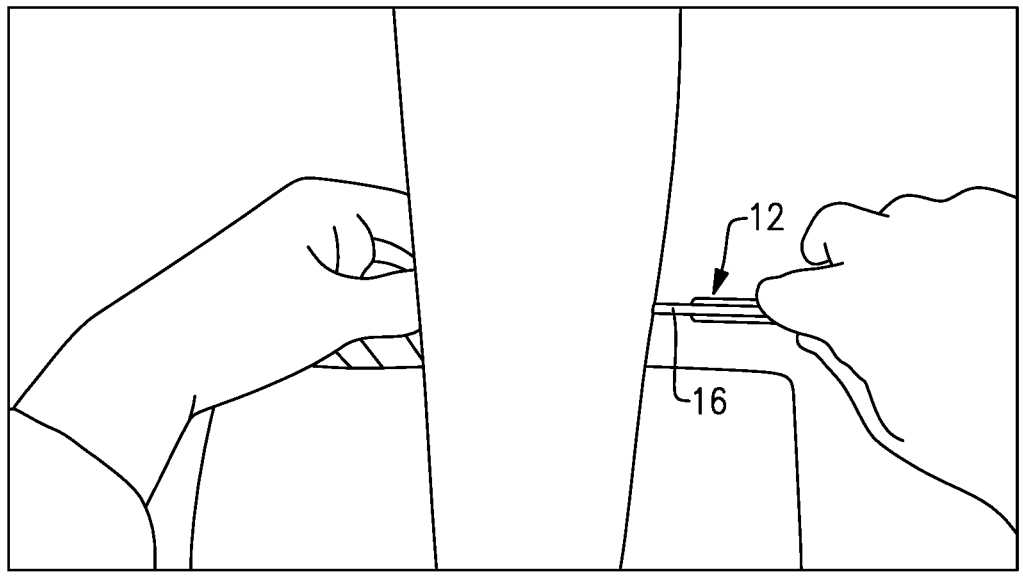

As shown in FIG. 12, the plane finder probe 16 may then be inserted into the slotted cannula 12 on the side of the medial incision 40 or the lateral incision 46. The plane finder probe 16 is used to establish the correct cutting plane for cutting the gastrocnemius aponeurosis during the release procedure. The angled portion 38 of the plane finder probe 16 may be used to dissect tissue 55 as it is passed medially or laterally through the slotted cannula 12 in order to establish the correct cutting plane. The slotted cannula 12 is then reintroduced over the plane finder probe 16 (in a medial to lateral direction, or vice versa) to align the slotted cannula 12 along the correct cutting plane (see FIG. 13). The plane finder probe 16 may then be removed.

Figure 14:
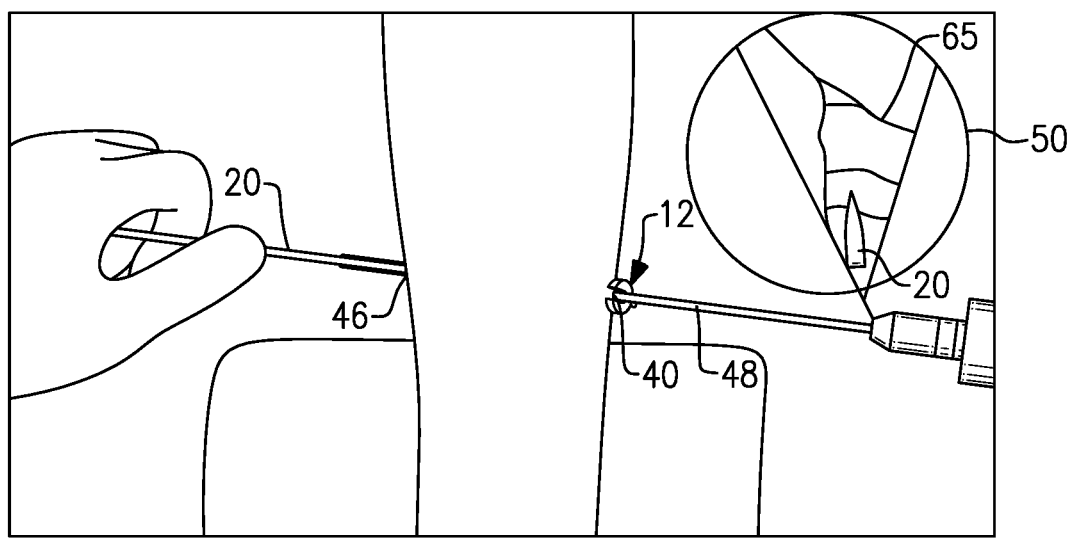

Referring now to FIG. 14, the endoscope 48 is positioned through the slotted cannula 12 on the side of the medial incision 40 and one of the cutting blades 20 is inserted through the slotted cannula 12 on the side of the lateral incision 46. The cutting blade 20 may then be used to dissect a portion of the gastrocnemius-soleus fascia 65 (see arthroscopic window 50 of FIG. 14).

Figure 15:
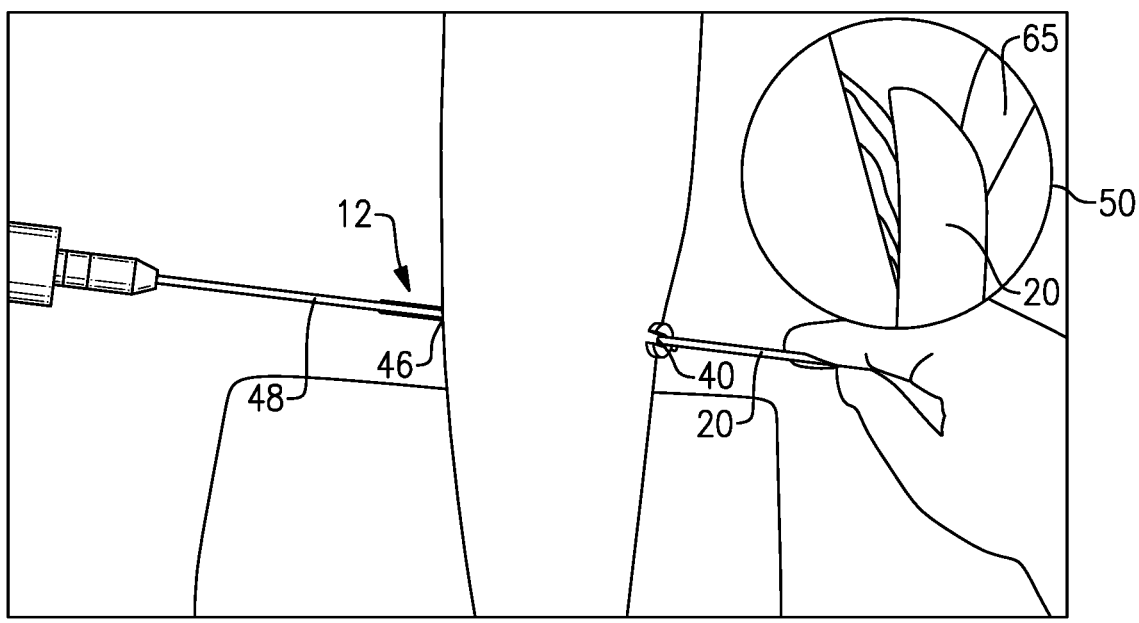

Finally, as shown in FIG. 15, the endoscope 48 may be inserted into the slotted cannula 12 on the side of the lateral incision 46 and the cutting blade 20 may be inserted on the side of the medial incision 40. Additional cuts can then be made in the gastrocnemius-soleus fascia 65 by moving the cutting blade 20 laterally to medially. In another embodiment, the cutting blade 20 is used to make cuts first through the lateral incision 46 before making cuts through the medial incision 40.

The cutting operations described above lengthen the gastrocnemius muscle. Lengthening of the gastrocnemius muscle is designed to alleviate pain by lowering the pressure at the front of the foot, improve foot function, decrease deformity, and prevent recurrence of foot problems.

FIGS. 16-21 illustrate an exemplary planar fascia release procedure that may be performed using the surgical system 10 of FIGS. 1-4. These figures illustrate, in sequential order, a non-limiting embodiment for performing an endoscopic plantar fascia release procedure. It should be understood; however, that fewer or additional steps than are recited below could be performed and that the recited order of steps is not intended to limit this disclosure. In an embodiment, the plantar fascia release procedure is an endoscopic procedure.

Figure 16:
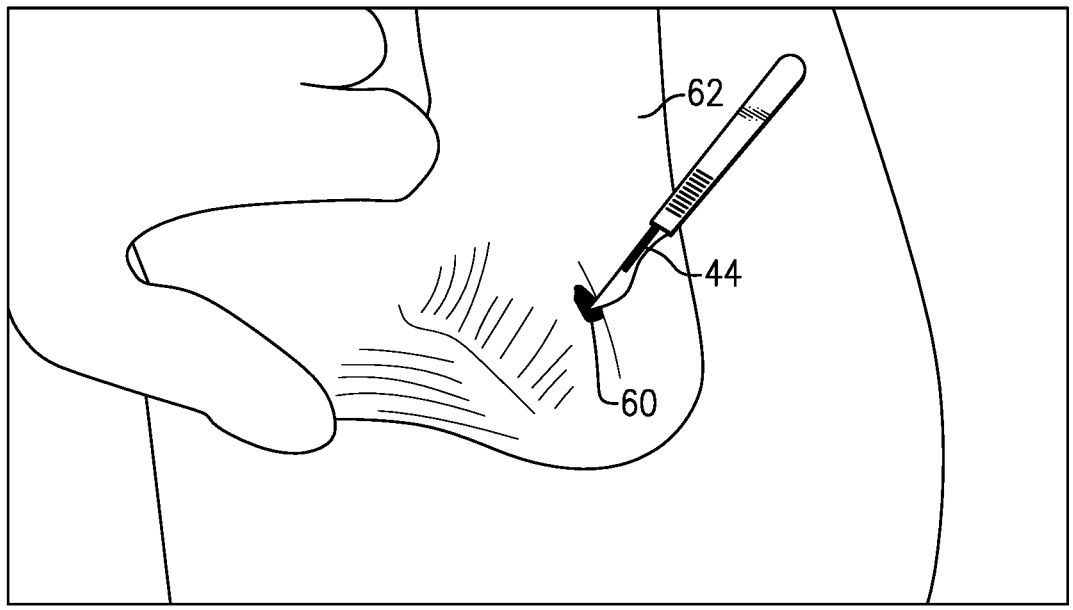
FIGS. 16, 17, 18, 19, 20, and 21 schematically illustrate an exemplary plantar fascia release procedure.

Referring first to FIG. 16, a medial incision 60 is made in a patient's foot 62 using a scalpel 44. The medial incision 60 may be made just anterior to the anterior portion of the calcaneus bone of the foot 62 and slightly medial to a medial band of the plantar fascia. This location may be marked on the foot 62 prior to making the medial incision 60.

Figure 17:
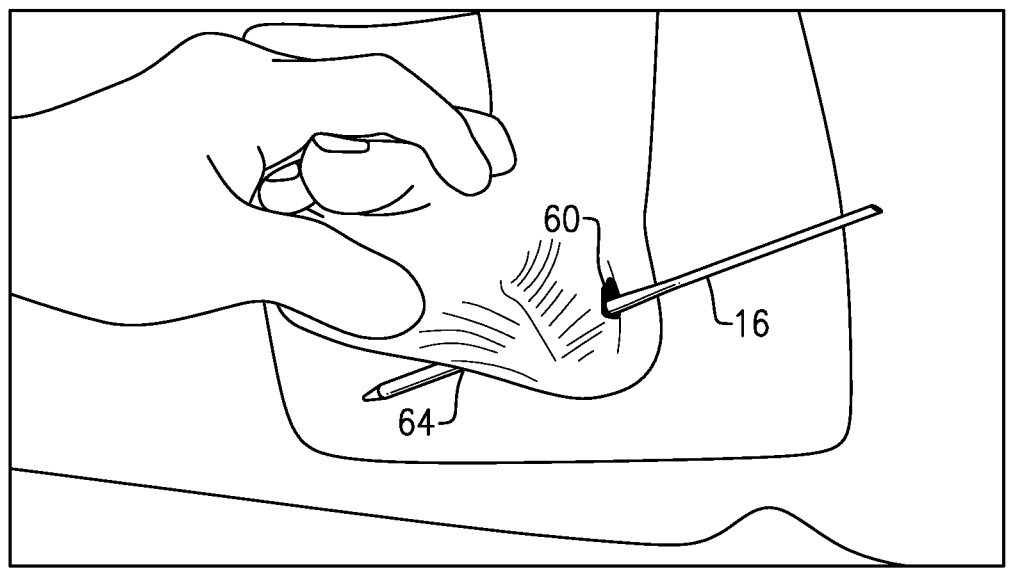

Next, as shown in FIG. 17, the plane finder probe 16 (or, alternatively, the trocar 14), is inserted through the medial incision 60 and then moved laterally until it reaches the opposite side of the soft tissue space (i.e., just under the skin on the lateral side of the foot 62). The plane finder probe 16 may be used to palpate the skin to mark the location for creating a lateral incision 64. The scalpel 44 is then used to create the lateral incision 64. The plane finder probe 16 may then be moved so that it extends through both the medial incision 60 and the lateral incision 64. In this position, the plane finder probe 16 establishes the correct cutting plane for cutting the plantar fascia during the release procedure.

Figure 18:
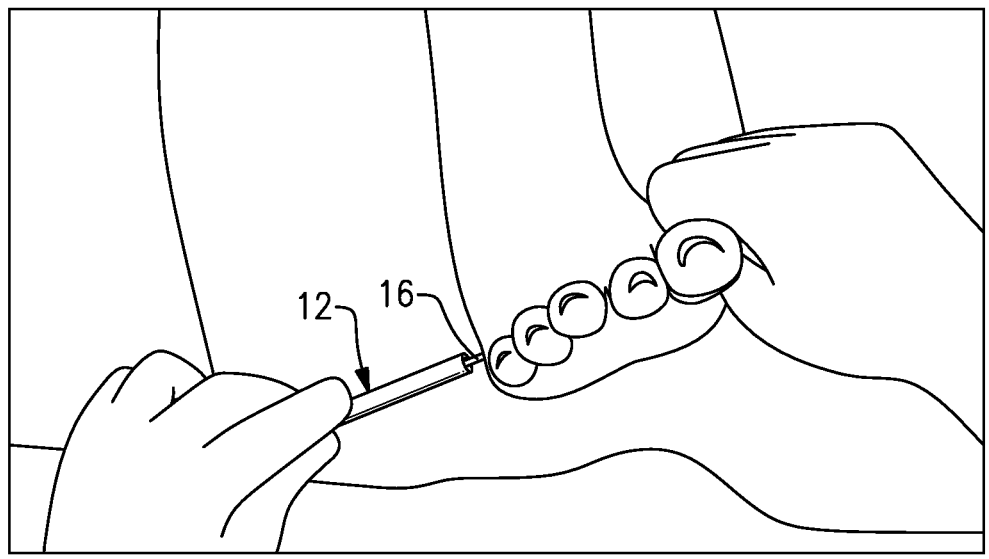

Referring now to FIG. 18, the slotted cannula 12 is introduced over the plane finder probe 16 (in a lateral to medial direction) to align the slotted cannula 12 along the correct cutting plane. The plane finder probe 16 may then be removed.

Figure 19:
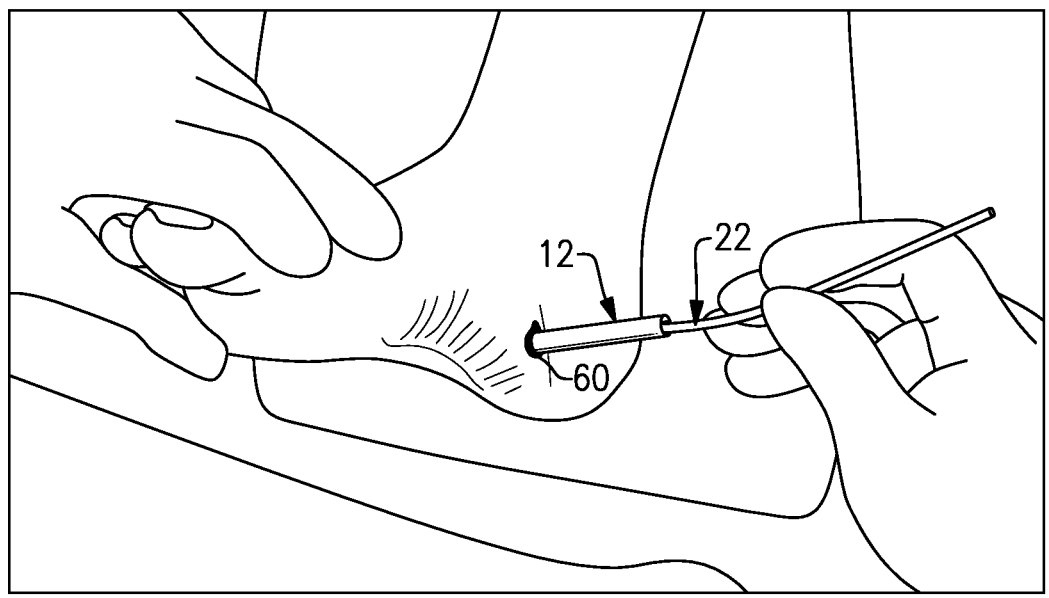

As shown in FIG. 19, the swabbing devices 22 may be used to clean the soft tissue space of any fluid, tissue, blood, etc., that could inhibit visualization during the procedure. The swabbing devices 22 are passed in a single direction (here, medially to laterally) through the slotted cannula 12 to avoid leaving any debris within the soft tissue space.

Figure 20:
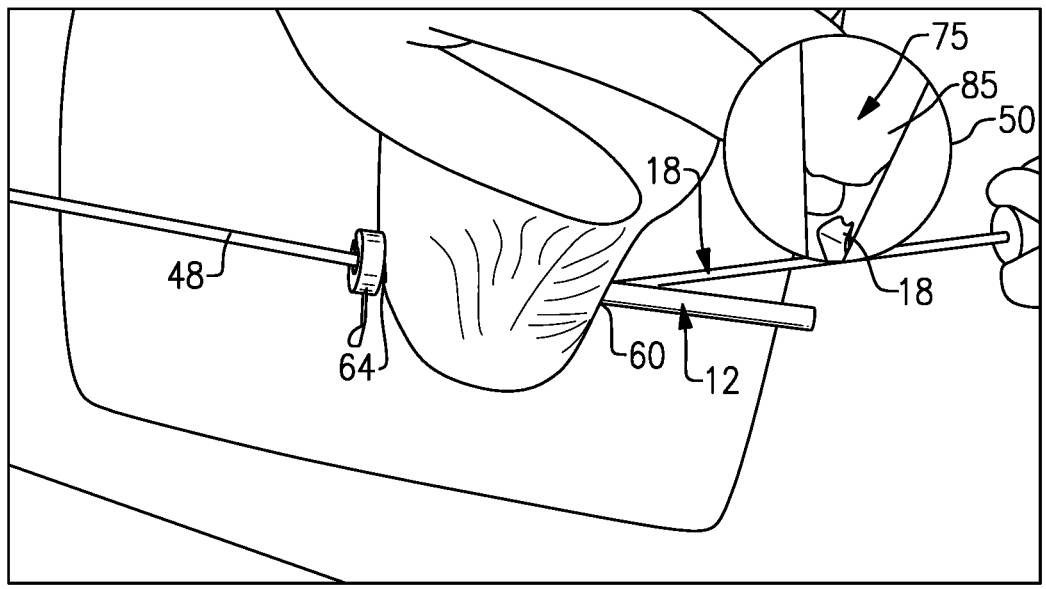

FIG. 20 illustrates the positioning of an endoscope 48 positioned through the slotted cannula 12 on the side of the lateral incision 64. The endoscope 48 provides direct visualization of the soft tissue space 75, via an arthroscopic window 50, through the translucent, slotted cannula 12. The rasp 18 may then be inserted into the slotted cannula 12 on the side of the medial incision 60. The rasp 18 is used to remove fatty layers 85 that may cover the plantar fascia. The rasp 18 is removed once visualization of the plantar fascia is sufficient.

Figure 21:
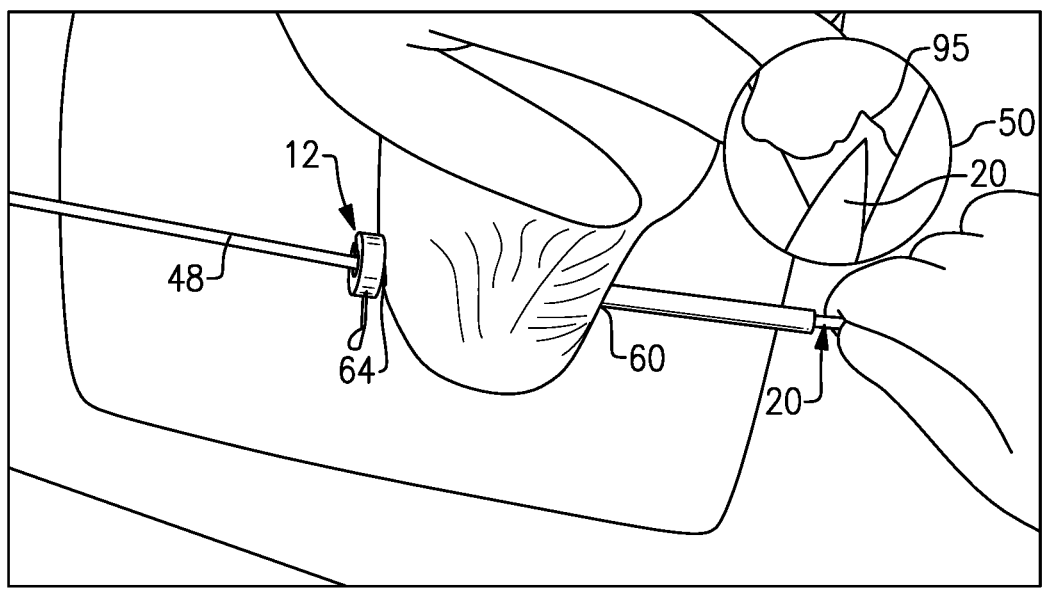

Finally, as illustrated in FIG. 21, one of the cutting blades 20 is inserted through the slotted cannula 12 on the side of the medial incision 60. The cutting blade 20 may then be used to dissect a portion of the plantar fascia 95. In an embodiment, a central band of the plantar fascia 95 is recessed but a lateral band of the plantar fascia 95 is left intact. The cutting operations described above remove or release the diseased portions of the plantar fascia that are responsible for the foot pain.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical system, comprising:
    a plane finder probe adapted to establish a cutting plane for resecting an anatomical structure,
    wherein the plane finder probe includes a non-threaded probe body that extends between a blunt ended portion and an angled end portion;
    a slotted cannula insertable over the plane finder probe to position the slotted cannula along the cutting plane; and
    a trocar insertable through the slotted cannula.

2. The surgical system as recited in claim 1, wherein the probe body tapers from the blunt ended portion toward the angled end portion.

3. The surgical system as recited in claim 1, wherein the plane finder probe is positionable within a slot of the slotted cannula.

4. The surgical system as recited in claim 1, wherein the slotted cannula is made from a transparent material.

5. The surgical system as recited in claim 1, wherein the slotted cannula extends along a longitudinal axis between a proximal end portion and a distal end portion.

6. The surgical system as recited in claim 5, comprising a hub disposed at the proximal end portion and including a central aperture sized to accommodate another surgical instrument.

7. The surgical system as recited in claim 6, comprising a handle that extends from the hub.

8. The surgical system as recited in claim 6, wherein the central aperture connects to a passage that extends through an outer peripheral surface of the hub.

9. The surgical system as recited in claim 1, comprising a swabbing device insertable through the slotted cannula.

10. The surgical system as recited in claim 1, comprising an endoscope insertable at a first side of the slotted cannula and a cutting blade insertable at a second side of the slotted cannula.

11. The surgical system as recited in claim 1, wherein the plane finder probe is a handle-less device.

12. A method for performing an endoscopic release procedure, comprising:
inserting the plane finder probe of the surgical system of claim 1 into a soft tissue space to establish the cutting plane for resecting the anatomical structure;
inserting the slotted cannula over the plane finder probe to position the slotted cannula along the cutting plane;
removing the plane finder probe;
inserting a cutting blade into the slotted cannula; and
resecting the anatomical structure along the cutting plane with the cutting blade.

13. The method as recited in claim 12, wherein the endoscopic release procedure is a gastrocnemius release procedure.

14. The method as recited in claim 12, wherein the endoscopic release procedure is a plantar fascia release procedure.

15. The method as recited in claim 12, comprising, prior to inserting the plane finder probe:
making a first incision at a first location associated with the soft tissue space;
inserting an assembly of a trocar and the slotted cannula through the first incision;
palpating skin associated with the soft tissue space using the trocar to mark a second location of a second incision; and
making the second incision at the second location.

16. The method as recited in claim 12, comprising:
inserting an endoscope into a first side of the slotted cannula; and
wherein inserting the plane finder probe includes inserting the plane finder probe into a second side of the slotted cannula.

17. The method as recited in claim 12, comprising:
inserting an endoscope into a first side of the slotted cannula; and
wherein inserting the cutting blade through the slotted cannula includes inserting the cutting blade into a second side of the slotted cannula.

18. The method as recited in claim 17, comprising:
inserting the endoscope into the second side of the slotted cannula;
inserting the cutting blade into the first side of the slotted cannula; and
making additional cuts in the anatomical structure with the cutting blade.

19. The method as recited in claim 12, comprising:
making a first incision at a first location of the soft tissue space prior to inserting the plane finder probe;
inserting the plane finder probe through the first incision;
palpating skin with the plane finder probe to mark a second location of a second incision; and
making the second incision at the second location.

20. The method as recited in claim 19, comprising:
moving the plane finder probe so it extends through both the first incision and the second incision; and
inserting the slotted cannula over the plane finder probe after moving the plane finder probe through both the first incision and the second incision.

21. A surgical system, comprising:
a plane finder probe adapted to establish a cutting plane for resecting an anatomical structure,
the plane finder probe including a probe body that extends between a blunt ended portion and a non-threaded angled end portion;
a slotted cannula insertable over the plane finder probe to position the slotted cannula along the cutting plane,
wherein the slotted cannula is made of a transparent material;
a trocar insertable into the slotted cannula,
the trocar including a tapered tip;
a rasp;
a first cutting blade insertable into the slotted cannula; and
a second cutting blade insertable into the slotted cannula,
wherein the first cutting blade includes a first cutting blade tip that is different from a second cutting blade tip of the second cutting blade.

* * * * *